(12) United States Patent
Allard et al.

(10) Patent No.: US 6,458,136 B1
(45) Date of Patent: Oct. 1, 2002

(54) ORTHOPAEDIC INSTRUMENT FOR SIZING IMPLANT SITES AND FOR PRESSURIZING BONE CEMENT AND A METHOD FOR USING THE SAME

(75) Inventors: Randy Allard, Plymouth, IN (US); Louis U. Bigliani, Englewood, NJ (US); Evan Flatow, New York, NY (US); John Meyers, Columbia City, IN (US); Terry Schlotterback; David Willard, both of Warsaw, IN (US)

(73) Assignee: Zimmer, Inc., Warsaw, IN (US)

( * ) Notice: Subject to any disclaimer, the term of this patent is extended or adjusted under 35 U.S.C. 154(b) by 0 days.

(21) Appl. No.: 09/568,695

(22) Filed: May 11, 2000

(51) Int. Cl.[7] ............................................. A61B 17/56
(52) U.S. Cl. ...................................................... 606/92
(58) Field of Search ............................. 606/53, 86, 92, 606/93, 94, 102; 623/908, 914, 22.12

(56) References Cited

U.S. PATENT DOCUMENTS

| | | | |
|---|---|---|---|
| 3,889,665 A | * | 6/1975 | Ling et al. ..................... 606/94 |
| 4,593,685 A | | 6/1986 | McKay |
| 4,595,006 A | * | 6/1986 | Burke et al. ................... 606/94 |
| 5,897,560 A | * | 4/1999 | Johnson ....................... 606/102 |
| 5,910,172 A | * | 6/1999 | Penenberg .................... 606/86 |
| 6,017,350 A | * | 1/2000 | Long ............................. 606/94 |
| 6,019,766 A | * | 2/2000 | Ling et al. ..................... 606/94 |

OTHER PUBLICATIONS

CMW Laboratories, Cement Pressurisation, Brit. JBJS, May 1990.
Jo Miller, M.D., Improved Fixation in Total Hip Arthroplasty, 1980.
Howmedica, Bone Cement Accessories & Surgical Simplex P Bone Cement, 1983.
Richards, Cement Compresors and Brushes, 1983.

* cited by examiner

Primary Examiner—Jeffrey A. Smith
Assistant Examiner—Eduardo C. Robert
(74) Attorney, Agent, or Firm—Jacque R. Wilson, Esq.

(57) ABSTRACT

An orthopaedic instrument and a method for its use in sizing a glenoid implant anchor site and for pressurizing bone cement in the anchor site. The instrument has a shaft with a handle on one end thereof and a pressure plate on the other end thereof. An implant site probe, corresponding in shape to the glenoid implant anchor, extends outwardly from a bone facing surface of the pressure plate. A seal against the bone facing surface surrounds the implant site probe. Forcing the implant site probe into the implant site filled with bone cement forces bone cement into the cancellous bone surrounding the implant site.

20 Claims, 4 Drawing Sheets

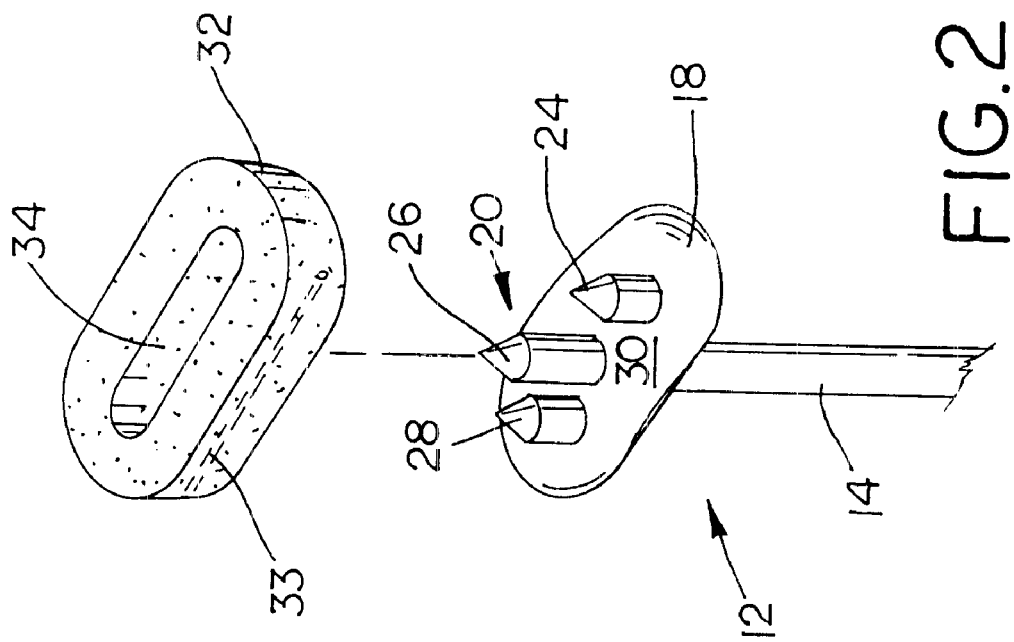
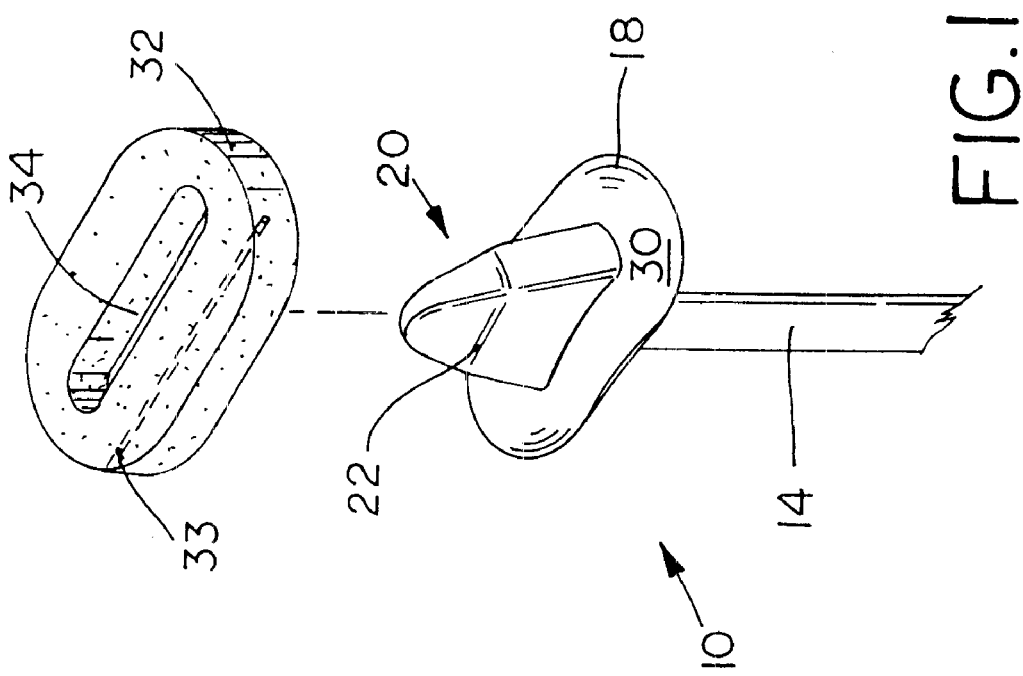

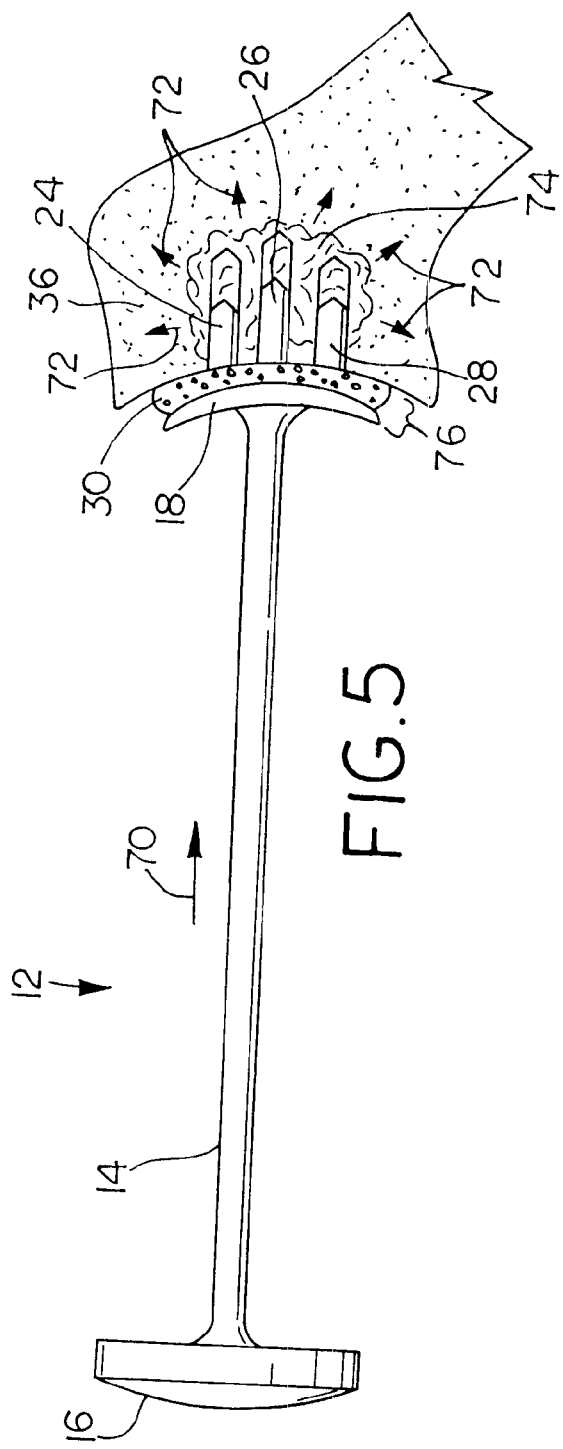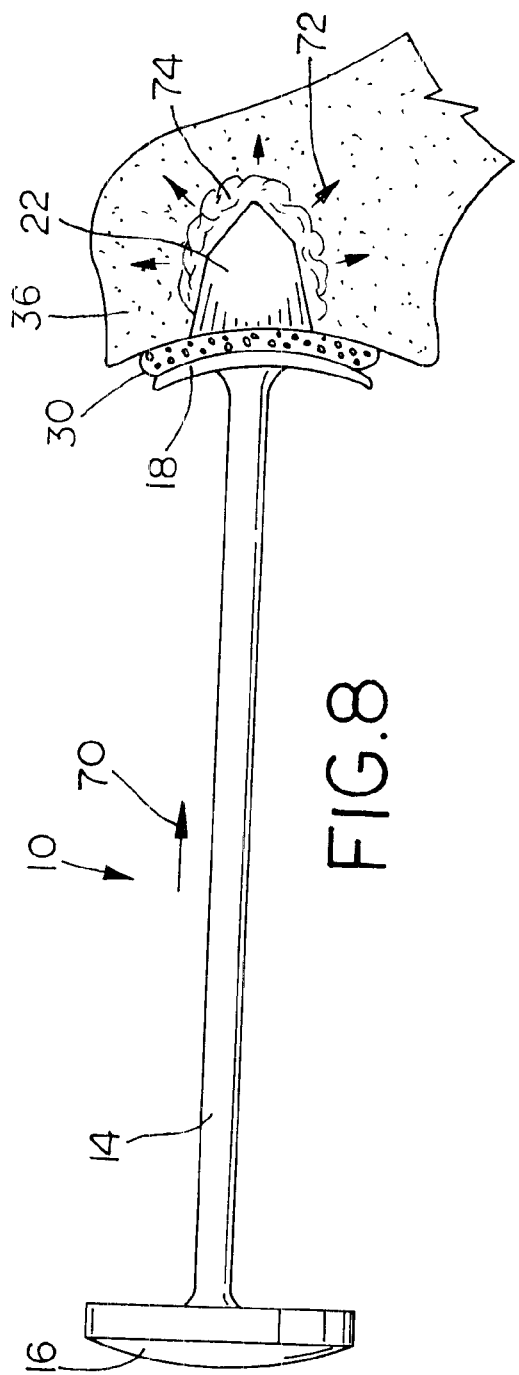

ORTHOPAEDIC INSTRUMENT FOR SIZING IMPLANT SITES AND FOR PRESSURIZING BONE CEMENT AND A METHOD FOR USING THE SAME

BACKGROUND OF THE INVENTION

1. Field of the Invention

The present invention relates to instruments used for orthopaedic surgical procedures, and, more particularly, to an instrument for sizing holes made in bones for receiving implants and for pressurizing bone cement used for securing the implants in the holes.

2. Description of the Related Art

Total shoulder arthroplasty is a complicated orthopaedic procedure involving replacement of the humeral and glenoid components of the joint. Replacement of the glenoid component remains one of the more difficult aspects of the procedure. The glenoid labram is excised and the surface debrided of cartilage and soft tissue remnants. The prosthetic implant includes anchoring components inserted into holes prepared in the remaining bone of the scapula. Bone cement is used to affix the implant anchors in place in the prepared anchor holes.

While the shoulder does not frequently support the full weight of a persons body, and, therefore, may not be thought of as a heavy load bearing joint, the force exerted on the shoulder joint through normal use of the arm can be quite high. Stability of the joint, after total shoulder arthroplasty, relies on many factors, including the proper attachment of the glenoid prosthesis at the anchor site. Unstable attachment of the glenoid prosthesis can lead to later joint function difficulties. Bone cements have been developed to improve bonding between the bone and the anchoring components of the prosthesis. The implants themselves have been improved in design, with ridges or grooves on the anchoring components, to enhance bonding and adherence between the bone cement and the implant.

For a proper bond, a proper hole size must be formed. The anchors of the implant are inserted into holes in the bone, and must fit properly for the strongest bond. Known glenoid prosthesis anchoring components include a plurality of pegs or a keel, inserted into prepared holes in the bone. Holes for the anchoring components are prepared by drilling into the bone, using a template as a guide for proper location of the holes. Proper width and depth, or shape of the hole or holes requires proper tool selection and use.

Bone cement delivery guns have been utilized to promote the effectiveness of implant fixation by improving penetration of the bone cement into the cancellous bone. Ratchet operated guns delivering a consistent flow of bone cement through properly sized and fitted nozzles are known.

What is needed is an orthopaedic instrument which is simple and easy to use, to pressurize bone cement in a prepared hole for the anchors of an implant, improving penetration of the bone cement into the surrounding cancellous bone.

What is further needed is an orthopaedic instrument suitable for proper sizing of holes to receive orthopaedic implants.

SUMMARY OF THE INVENTION

The present invention provides an orthopaedic instrument and a method for using the instrument, to verify that a proper anchor hole has been created, and to pressurize bone cement in the prepared holes, forcing bone cement into the surrounding cancellous bone.

The present invention comprises, in one form thereof, an orthopaedic instrument having a shaft, a pressure plate on one end of the shaft, a bone facing surface on the pressure plate, and an implant anchor site probe extending outwardly from the bone facing surface of the pressure plate. A removable seal may be placed around the anchor site probe, against the pressure plate.

The invention comprises, in another form thereof, an orthopaedic bone cement pressurizer having a shaft with a first end and a second end. A pressure plate is disposed on the first end of the shaft, and includes a bone side surface. An implant anchor site probe extends outwardly from the bone side surface of the pressure plate. A seal is disposed against the bone side surface of the pressure plate, and forms a seal surrounding the implant anchor site probe.

The invention comprises, in yet another form thereof, an orthopaedic procedure for inserting an implant, comprising preparing a bone site to receive a prosthetic implant, including forming one or more implant anchor component receiving holes at the prepared bone site, depositing bone cement in the receiving holes; providing an instrument having an implant anchor site probe shaped similarly to implant anchor components of the prosthetic implant to be used; forcing the implant anchor site probe into the receiving holes; removing the implant anchor site probe; and implanting the prosthesis.

An advantage of the present invention is providing an orthopaedic instrument, which will consistently and uniformly pressurize bone cement in a hole prepared to receive an implant.

Another advantage of the present invention is providing an instrument and method for consistently and uniformly impregnating cancellous bone with bone cement for attaching a prosthesis.

Yet another advantage of the present invention is providing a surgical procedure for gauging proper size of a prosthetic implant site and pressurizing bone cement in the site.

A still further feature of the present invention is providing an orthopaedic bone cement pressurizing instrument which is easy to use and not prone to failure.

BRIEF DESCRIPTION OF THE DRAWINGS

The above-mentioned and other features and advantages of this invention, and the manner of attaining them, will become more apparent and the invention will be better understood by reference to the following description of the embodiments of the invention taken in conjunction with the accompanying drawings, wherein:

FIG. 1 is an exploded perspective view of one embodiment of the present invention for use with a keeled glenoid implant;

FIG. 2 is an exploded perspective view of a second embodiment of the present invention, for use with a pegged glenoid implant;

FIG. 5 is an illustration of the manner of using the embodiment of the present invention shown in FIG. 2, for pressurizing bone cement for a pegged glenoid implant;

FIG. 8 is an illustration of the manner of using the embodiment of the present invention shown in FIG. 1, for pressurizing bone cement for a keeled glenoid implant.

Corresponding reference characters indicate corresponding parts throughout the several views. The exemplifications set out herein illustrate preferred embodiments of the invention, and such exemplifications are not to be construed as limiting the scope of the invention in any manner.

DETAILED DESCRIPTION OF THE INVENTION

Figure 3:
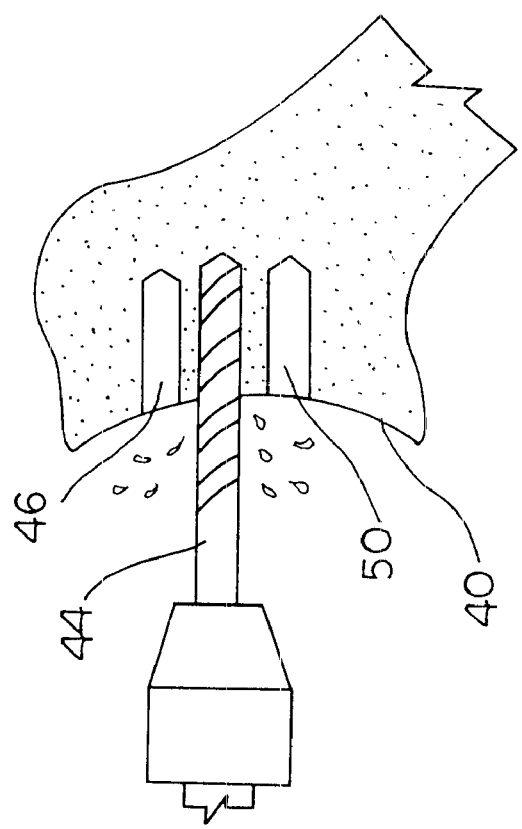
FIG. 3 is an illustration of the manner of preparing a site for receiving a pegged glenoid implant.

Referring now more specifically to the drawings, and to FIGS. 1 and 2 in particular, a keeled glenoid implant bone cement pressurizer 10 (FIG. 1), and a pegged glenoid implant bone cement pressurizer 12 (FIG. 2) are shown. Bone cement pressurizers embodying the present invention are particularly advantageous in use for implanting a glenoid prosthesis; however, it should be understood that the concepts of the present invention can be applied to use in other implant procedures as well. Bone cement pressurizers 10 and 12 are similar, except for modifications to adapt each for use with a specific type or style of glenoid implant.

Bone cement pressurizers 10 and 12 each include a shaft 14 and a knob or handle 16 (FIGS. 5 and 8). Shaft 14 need only be sufficiently long for ease in handling bone cement pressurizer 10 or 12. The shape and configuration of handle 16 may differ. For some, a knob such as shown in FIGS. 5 and 8 is suitable, convenient and easy to use. Others may prefer a more elongated structure to fit in the palm of the hand. The length of shaft 14, and the configuration of handle 16, may differ in bone cement pressurizers used for other types of implants, and for implants at other joint sites. The purpose of each is for proper manipulation and use of the instrument, including proper insertion and application of pressure, as will be described in greater detail hereinafter.

Each of bone cement pressurizer 10 and bone cement pressurizer 12 includes a pressure plate 18 and an implant anchor site probe 20 extending outwardly from pressure plate 18. In the preferred embodiments, the anchor site probe 20 is an elongate member extending from the pressure plate 18 generally parallel to the shaft 14 and perpendicular to the pressure plate 18. In the embodiment of the invention shown in FIG. 1, implant anchor site probe 20 takes the form of a keel 22, similar in size and shape to the keel anchor component of a keeled glenoid implant. Preferably the anchor site probe 20 is the same size and shape as the keel anchor component. In the embodiment of the invention shown in FIG. 2, implant anchor site probe 20 takes the form of three pegs 24, 26 and 28, which are similar in size, shape and positioning relative to each other to duplicate the implant anchor components of a pegged glenoid implant. Preferably the pegs have the same size, shape, and position as the implant anchor components. For use with other types of implant anchor components, implant anchor site probe 20 will differ from the keel 22 and pegs 24, 26 and 28 embodiments shown, and will conform to the implant anchor component being used. Implant anchor site probe 20 extends outwardly from a bone facing surface 30 of pressure plate 18, generally on the opposite side of pressure plate 18 from shaft 14.

Shaft 14, handle or knob 16, pressure plate 18 and implant anchor site probe 20 may be made of any suitable strong surgical instrument grade material. Advantageously, the surfaces of implant anchor site probe 20 and bone facing surface 30 of pressure plate 18 will be highly polished, to minimize the adherence of bone cement thereto.

When pressurizing bone cement in a suitable site, a pressure seal or sponge 32 is provided between bone facing surface 30 of pressure plate 18 and the bone receiving the implant, to act as a seal during the pressurization step, as will be described in greater detail hereinafter. Seal 32 is oval shaped, generally conforming in size to bone facing surface 30 of pressure plate 18. Seal 32 defines therein a central opening 34, and surrounds implant anchor site probe 20 when properly positioned with probe 20 extending through central opening 34. Seal 32 is preferably made of a soft, highly compressible material. A crosslinked, closed cell polyethylene foam material has been found to be particularly well suited to this application. Seal 32 preferably contains an x-ray flag 33, such as a small strip of material which will register on an x-ray. Preferably, the x-ray flag 33 comprises a barium sulfate impregnated thread imbedded in the soft foam body of the seal 32. The x-ray flag 33 enables the seal 32 to be detected by x-ray to ensure its removal from the surgical site.

Figure 7:
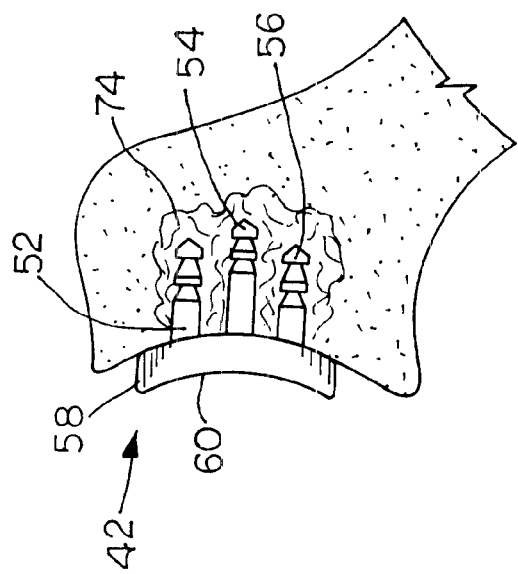
FIG. 7 is an illustration of the implanted pegged glenoid implant.
Figure 6:
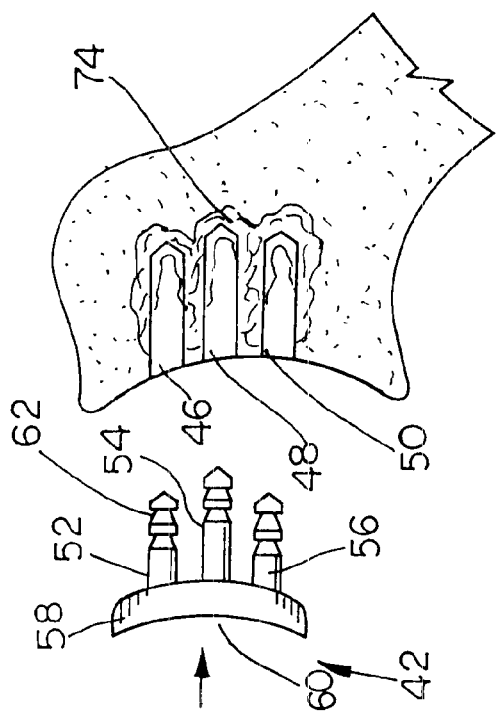
FIG. 6 is an illustration of the implant procedure for a pegged glenoid implant.

In FIG. 3, the preparation of a site on a glenoid 36 for receiving a pegged glenoid implant is shown. A site surface 40 of the glenoid is prepared and, for a pegged glenoid implant 42 (FIG. 6 and FIG. 7) a bone drill 44 is used to create holes in the glenoid for receiving the implant. It is known to use a template (not shown) to properly position each of three receiving holes 46, 48 and 50, to receive peg anchor components 52, 54 and 56 of pegged glenoid implant 42. Pegged glenoid implant 42 further includes a body 58 having a glenoid joint surface 60. Pegs 24, 26 and 28 of pegged glenoid implant bone cement pressurizer 12 should be similar in length, width and configuration to peg anchor components 52, 54 and 56 of pegged glenoid implant 42. While pegs 24, 26 and 28 of pegged glenoid implant bone cement pressurizer 12 are essentially smooth on the outer surface thereof, peg anchor components 52, 54 and 56 of glenoid implant 42 may have a series of ridges or grooves 62 formed therein, or have other surface irregularities to improve adherence between peg anchor components 52, 54, 56 and bone cement 64 used in holes 46, 48 and 50. Bone cement 64 may be provided to holes 46, 48 and 50 by a syringe like applicator, 66 having a needle or other nozzle structure 68 thereon for delivering bone cement 64 directly into each receiving hole 46, 48 and 50 at the site of the implant.

Figure 4:
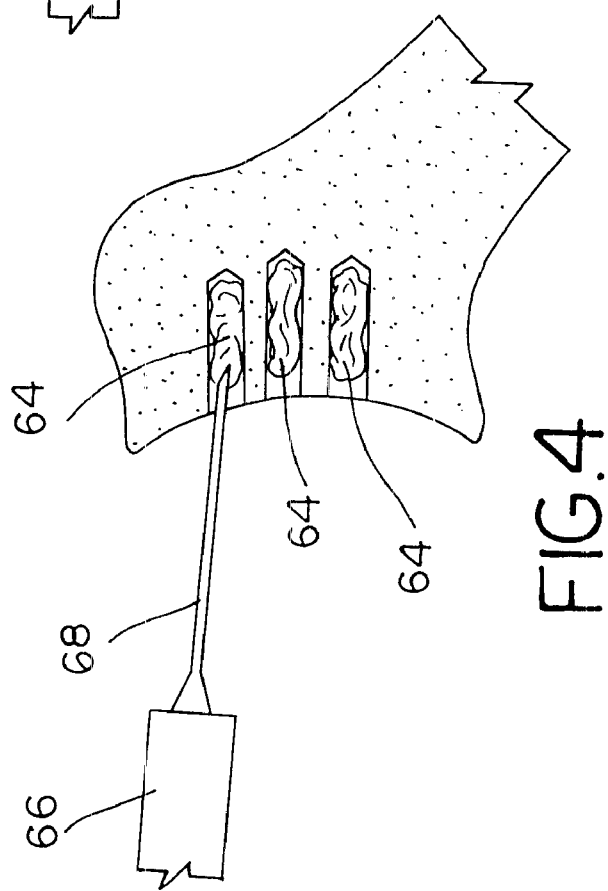
FIG. 4 an illustration of a further step in the procedure for preparing the site illustrated in FIG. 3.

As shown in FIG. 4, after holes 46, 48 and 50 have been properly prepared, each is filled with bone cement 64 from applicator 66. Sponge seal 32 is placed around pegs 24, 26 and 28 of pegged glenoid implant bone cement pressurizer 12. Sponge seal 32 rests against bone facing surface 30 of pressure plate 18, with pegs 24, 26 and 28 extending through central opening 34 of sponge seal 32. Pressurizer 12 is positioned with pegs 24, 26 and 28 aligned with holes 46, 48 and 50. Pressure is exerted on shaft 14 via handle 16, or the like, in the direction indicated by the arrow 70. As pegs 24, 26 and 28 are forced into holes 46, 48 and 50, bone cement 64 contained in holes 46, 48 and 50 is forced outwardly as indicated by arrows 72, into the cancellous bone, forming a substantially continuous cement mantle 74 in the cancellous bone. Seal 32 allows pressure to build in each of the holes 46, 48 and 50 as pressurizer 12 is forced in the direction indicated by arrow 70, thus forcing cement into the cancellous bone. Seal 32 reduces the escape of cement from holes 46, 48 and 50.

In a preferred structure for bone cement pressurizer 10, 12, pressure plate 18 is shaped in a curving manner, substantially similar to the curved prepared glenoid implant site surface 40. Pressure is supplied by bone cement pressurizer 10, 12 substantially normal to glenoid implant site surface 40, to maintain a consistently thick space 76 between glenoid implant site surface 40 and bone facing surface 30 of pressure plate 18, even as the thickness of space 76 diminishes as pressure is applied and seal 32 is compressed. Preferably the pressure plate 18 is at least as large as the backside of the corresponding glenoid implant 42. Likewise, it is preferable that the plate 18 supports all of the seal 32 so that the seal 32 is contained and pressed evenly against the bone. The softness of the seal 32 and the extensive support of the plate together provide an effective seal to prevent the escape of cement. As the anchor site probe 20 is inserted into the prepared site, the seal 32 makes contact with the bone and begins to seal the area surrounding the prepared site. At this initial position, the seal 32 is disposed against the bone facing surface 30 of the pressure plate 18 and surrounds the anchor site probe 20 so that a portion of the probe 20 is exposed or extends beyond the seal 32. Further pressure on the pressurizer 10 causes the seal 32 to compress to a second position nearer the bone facing surface 30 in which more of the anchor site probe 20 is exposed or more of the probe 20 extends from the compressed seal 32. Thus, the compressibility of the seal 32 permits further penetration of the anchor site probe 20 and pressurization of the cement while continuously providing a seal. Cement that may be initially displaced into the seal central opening 34 is forced back into the prepared site under pressure as the pressure plate 18 compresses the seal 32 and presses against the cement.

Once the cement has been adequately pressurized, pressurizer 12 is removed. Since pegs 24, 26, 28 are formed of highly polished steel or other material, minimal sticking of bone cement 64 to pegs 24, 26 and 28 will occur. In some instances, it may be desirable to then add additional bone cement to receiving holes 46, 48 and 50, and repeat the pressurization process, to force additional bone cement into the cancellous bone. Holes 46, 48 and 50 may again be filled with additional bone cement 64. After sufficient cement has been provided, peg anchor components 52, 54 and 56 of implant 42 are inserted into receiving holes 46, 48 and 50, and the implant is properly positioned and set in place in conventional manner.

Figure 9:
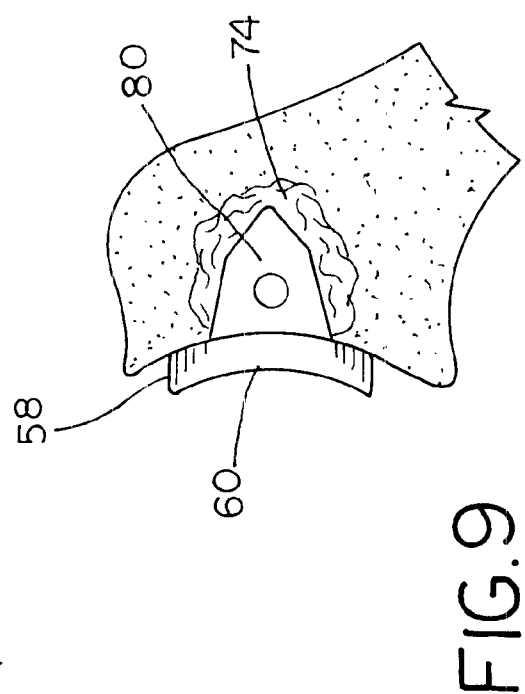
FIG. 9 is an illustration of the implanted keeled glenoid implant.

FIGS. 8 and 9 illustrate the manner of using bone cement pressurizer 10 for the implant of a keeled glenoid implant 80 (FIG. 9). An appropriately shaped hole is formed in known manner at glenoid implant site 40. Bone cement pressurizer 10 is prepared by placing seal 32 around keel 22 of keeled glenoid implant bone cement pressurizer 10, with keel 22 extending through central opening 34. In similar manner to that described for the use of pegged glenoid implant bone cement pressurizer 12, bone cement 64 is deposited in the keel shaped hole. Keel 22 is aligned with the hole, and is forced into the hole to pressurize bone cement 64 therein. Cement 64 is thereby forced into the surrounding cancellous bone, forming consistent cement mantle 74. Thereafter, keeled glenoid bone cement pressurizer 10 is removed, and additional bone cement 64 may be added and pressurized. When sufficient bone cement is in place, keel 82 of keeled glenoid implant 80 is inserted into the hole, perhaps with the addition of additional bone cement 64.

During preparation of the implant site, and particularly during the formation of the implant anchor component receiving hole or holes, such as receiving holes 46, 48 and 50, the corresponding, appropriate keeled glenoid implant bone cement pressurizer 10 or pegged glenoid implant bone cement pressurizer 12 may be used to ensure that the holes being formed for receiving the implant anchor components are of proper size, shape and depth. Implant anchor site probe 20 may be inserted into the anchor receiving hole or holes before bone cement 64 is added thereto. This "dry run" can be done without the placement of seal 32 against bone facing surface 30. If implant anchor site probe 20 is similarly shaped and sized to the anchoring component of the implant to be used, the "dry run" will ensure proper fit of the anchoring component in the receiving holes. The bone cement pressurizer 10, 12 thereby serves a dual purpose, as a hole sizer and as a bone cement pressurizer.

Either keeled glenoid implant bone cement pressurizer 10 or pegged glenoid implant bone cement pressurizer 12 may be reused after proper cleaning and sterilization. Sponge 32, however, is a disposable component, and will be discarded after each use, with a new one used for the next procedure.

Shapes other than the keeled shape and pegged shape shown, may be used to conform to the specific glenoid implant anchor components being used, or to the implant anchor components for other joint implants.

While this invention has been described as having a preferred design, the present invention can be further modified within the scope and spirit of this disclosure. This application is therefore intended to include and cover any and all variations, uses, or adaptations of the invention using its general principles. Further, this application is intended to cover such departures from the present disclosure as come within known or customary practice in the art to which this invention pertains and which fall within the limits of the appended claims.

What is claimed is:

1. An orthopaedic instrument comprising:
   a shaft having a first end and a second end;
   a pressure plate on one of said first end and said second end of said shaft, said pressure plate having a bone facing surface;
   an implant anchor site probe extending outwardly from said bone facing surface; and a seal disposed against said bone facing surface and surrounding said implant anchor site probe.

2. An orthopaedic instrument comprising;
   a shaft having a first end and a second end;
   a pressure plate on one of said first end and said second end of said shaft, said pressure plate having a bone facing surface; and an implant anchor site probe extending outwardly from said bone facing surface, comprising a plurality of legs.

3. An orthopaedic instrument as defined in claim 2, further comprising a seal disposed against said bone facing surface and surrounding said plurality of pegs.

4. An orthopaedic instrument as defined in claim 3, further comprising a handle on said shaft on an opposite end thereof from said pressure plate.

5. An orthopaedic bone cement pressurizer comprising:
   a shaft having a first end and a second end;
   a pressure plate disposed on said first end of said shaft, said pressure plate having a bone facing surface;
   an implant site probe extending outwardly from said bone facing surface of said pressure plate; and a seal disposed against said bone facing surface of said pressure plate, said seal forming a barrier surrounding said implant site probe.

6. An orthopaedic bone cement pressurizer as defined in claim 5, wherein said implant site probe is shaped to correspond to a shape of an anchor component of an orthopaedic implant.

7. An orthopaedic bone cement pressurizer as defined in claim 6, in which said implant site probe comprises a plurality of pegs.

8. An orthopaedic bone cement pressurizer as defined in claim 6, in which said implant site probe comprises a keel shaped body.

9. An orthopaedic bone cement pressurizer as defined in claim 5, in which said seal is adapted for placement on and removal from said pressure plate.

10. An orthopaedic bone cement pressurizer as defined in claim 9, in which said seal includes an x-ray flag.

11. An orthopaedic bone cement pressurizer as defined in claim 5, in which said bone facing surface of said pressure plate and said implant site probe are highly polished to minimize bone cement adherence.

12. A method for implanting a prosthetic joint component comprising:

preparing a bone site to receive an implant;

forming implant anchor component receiving holes at the prepared bone site;

depositing bone cement in the receiving holes;

providing an instrument having an implant anchor site probe shaped similarly to implant anchors of the implant to be used;

inserting the implant anchor site probe into the holes;

removing the implant anchor site probe; and implanting the implant.

13. The method of claim 12, comprising gauging the appropriateness of the implant anchor site holes by placing the implant anchor site probe into the implant anchor site hole before said step of depositing bone cement in the receiving holes.

14. The method of claim 12, further comprising adding additional bone cement to said receiving hole after removing the implant anchor site probe.

15. The method of claim 14, further comprising gauging the appropriateness of the implant anchor site holes by placing the implant anchor site probe into the implant anchor site hole before said step of depositing bone cement in the receiving holes.

16. The method of claim 12, further comprising reinserting the implant anchor site probe into the holes after said step of adding additional bone cement.

17. An orthopaedic instrument comprising:

a pressure plate, said pressure plate having a bone facing surface;

an implant anchor site probe extending outwardly from said bone facing surface; and a seal made of a compressible material disposed against said bone facing surface and surrounding said implant anchor site probe.

18. The instrument of claim 17 wherein the seal is compressible from an initial position in which a portion of the anchor site probe is exposed and a compressed position neared the facing surface in which more of the anchor site probe is exposed.

19. The instrument of claim 18 wherein the seal is generally the same size and shape as the facing surface such that the seal is fully supported by the facing surface.

20. The instrument of claim 17 further comprising an x-ray flag imbedded in the seal, the x-ray flag comprising a barium sulfate impregnated thread.

* * * * *